United States Patent
Philippon

(10) Patent No.: US 11,020,156 B2
(45) Date of Patent: *Jun. 1, 2021

(54) BONE IMPLANT

(71) Applicant: MJP INNOVATIONS, INC., Edwards, CO (US)

(72) Inventor: Marc Joseph Philippon, Vail, CO (US)

(73) Assignee: MJP Innovations, Inc., Edwards, CO (US)

( * ) Notice: Subject to any disclaimer, the term of this patent is extended or adjusted under 35 U.S.C. 154(b) by 33 days.

This patent is subject to a terminal disclaimer.

(21) Appl. No.: 16/379,951

(22) Filed: Apr. 10, 2019

(65) Prior Publication Data
US 2019/0290337 A1    Sep. 26, 2019

Related U.S. Application Data

(63) Continuation of application No. 14/297,783, filed as application No. PCT/IB2013/002066 on Sep. 20, 2013, now Pat. No. 10,265,107.
(Continued)

(51) Int. Cl.
*A61B 17/72*    (2006.01)
*A61B 17/74*    (2006.01)
(Continued)

(52) U.S. Cl.
CPC .......... *A61B 17/725* (2013.01); *A61B 17/742* (2013.01); *A61B 17/864* (2013.01);
(Continued)

(58) Field of Classification Search
CPC ............ A61B 17/72–7291; A61B 17/84–8695
See application file for complete search history.

(56) References Cited

U.S. PATENT DOCUMENTS 3,791,380 A * 2/1974 Dawidowski ........ A61B 17/746
606/68
4,644,943 A * 2/1987 Thompson ............. A61B 17/88
606/64
(Continued)

FOREIGN PATENT DOCUMENTS

WO    WO 2004/049963 A1    6/2004
WO    WO 2009/146457 A1    12/2009

OTHER PUBLICATIONS

International patent application No. PCT/IB2013/002066, International Search Report, dated Jan. 23, 2014.

*Primary Examiner* — Eduardo C Robert
*Assistant Examiner* — Steven J Cotroneo
(74) *Attorney, Agent, or Firm* — Da Vinci Partners LLC; John Moetteli

(57) ABSTRACT

A system and method for forming a hip implant offering minimal invasiveness is described. The system comprises means for positioning the implant under optical and X-ray control, an implant and an applicator for screwing and expanding the implant. The implant includes an insert body and an expansion tube with cut-outs and slits defining legs. The legs expand radially through windows in the insert body when the expansion tube is pushed against the sloped distal portion of the insert body. The expansion process may be ensured by using an anti-rotation device to prevent the insertion tube from rotating within the insert body. Applicator and implant are provided with means preventing cold welding during the implantation process.

15 Claims, 14 Drawing Sheets

Related U.S. Application Data

(60) Provisional application No. 61/703,327, filed on Sep. 20, 2012.

(51) Int. Cl.
*A61B 17/86* (2006.01)
*A61B 17/88* (2006.01)
*A61B 17/17* (2006.01)
*A61B 17/84* (2006.01)
*A61B 17/56* (2006.01)

(52) U.S. Cl.
CPC ...... *A61B 17/8685* (2013.01); *A61B 17/8872* (2013.01); *A61B 17/8891* (2013.01); *A61B 17/1742* (2013.01); *A61B 17/7266* (2013.01); *A61B 17/844* (2013.01); *A61B 17/862* (2013.01); *A61B 17/8615* (2013.01); *A61B 17/8625* (2013.01); *A61B 17/888* (2013.01); *A61B 17/8883* (2013.01); *A61B 2017/561* (2013.01); *A61B 2017/8655* (2013.01); *F04C 2270/041* (2013.01)

(56) References Cited

U.S. PATENT DOCUMENTS

| | | | |
|---|---|---|---|
| 5,849,004 A * | 12/1998 | Bramlet | A61B 17/0401 606/232 |
| 5,976,139 A * | 11/1999 | Bramlet | A61B 17/1721 606/66 |
| 6,319,255 B1 | 11/2001 | Grundei et al. | |
| 6,679,890 B2 | 1/2004 | Margulies et al. | |
| 7,070,601 B2 * | 7/2006 | Culbert | A61B 17/685 606/311 |
| 7,258,692 B2 * | 8/2007 | Thelen | A61B 17/1668 606/62 |
| 8,012,155 B2 | 9/2011 | Prygoski et al. | |
| 8,157,801 B2 * | 4/2012 | Doubler | A61B 17/7225 606/64 |
| 10,265,107 B2 * | 4/2019 | Philippon | A61B 17/8872 |
| 2004/0193162 A1 * | 9/2004 | Bramlet | A61B 17/746 606/66 |
| 2006/0064098 A1 * | 3/2006 | Hansson | A61B 17/744 606/62 |
| 2009/0112210 A1 | 4/2009 | Philippon et al. | |
| 2011/0238122 A1 * | 9/2011 | Gradl | A61B 17/8605 606/289 |

\* cited by examiner

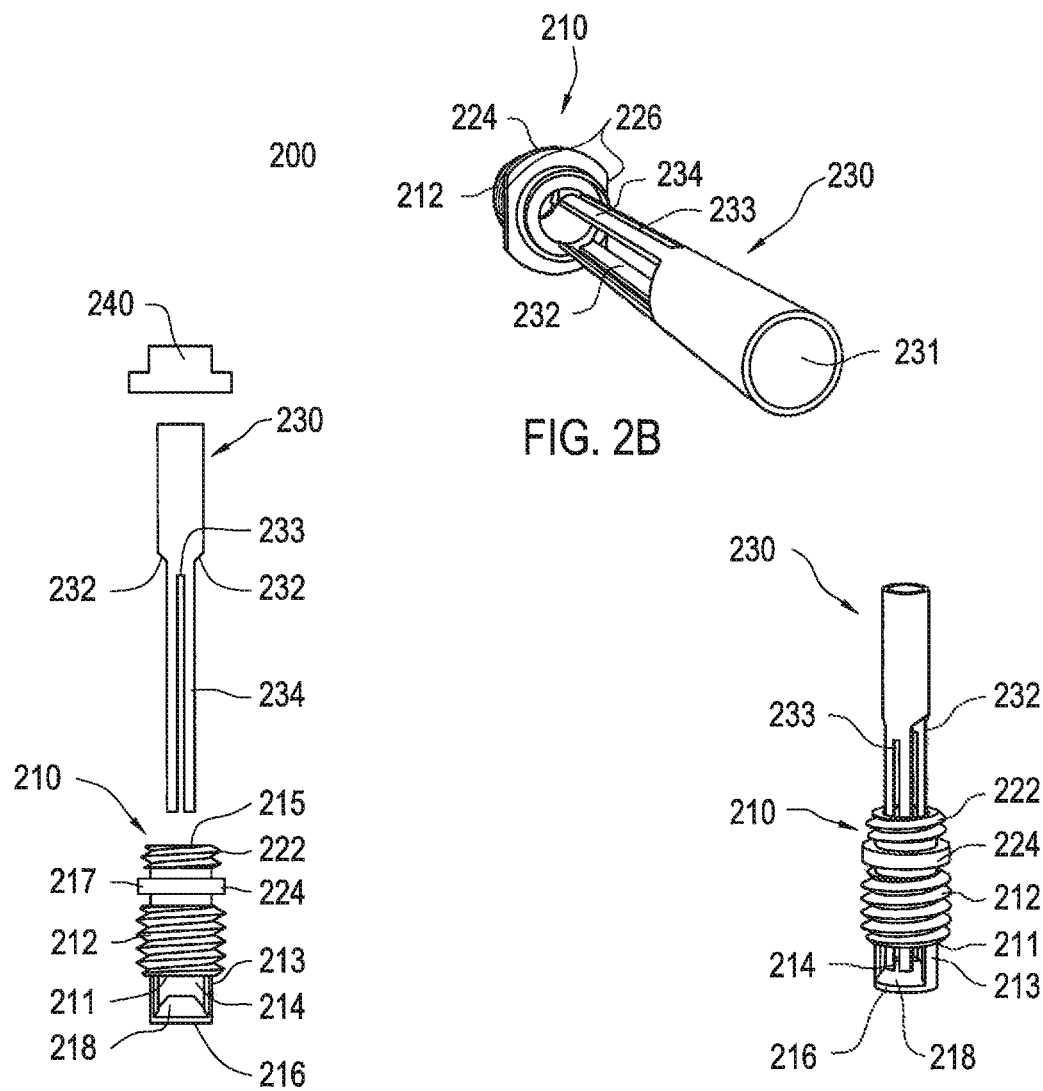
FIG. 2A
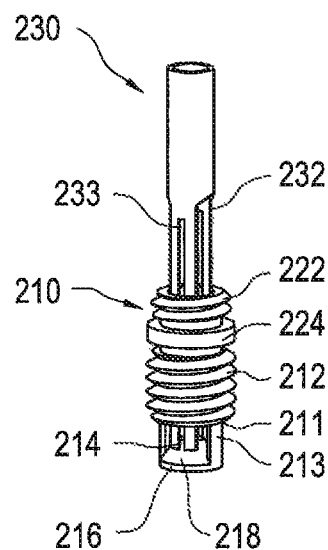
FIG. 2B
FIG. 2C
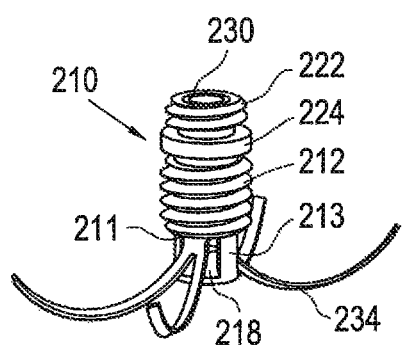
FIG. 2D

BONE IMPLANT

CROSS REFERENCE TO RELATED APPLICATIONS

The present application is a continuation in part application of U.S. patent application Ser. No. 14/429,783, filed Mar. 20, 2015, which is the national stage application of PCT/IB2013/002066, filed Sep. 20, 2013, which claims the benefit of prior filed U.S. Provisional Patent Application, Ser. No. 61/703,327 filed 20 Sep. 2012, which prior application is incorporated herein by reference.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

FIELD OF THE INVENTION

This invention relates to a system, devices and methods for bone reinforcement, especially for the treatment of osteoporosis.

BACKGROUND OF THE INVENTION

Osteoporosis, the reduction of bone density, is one of the major reasons for femoral neck fractures, affecting millions of elderly people worldwide each year. It is, however, increasingly becoming a problem also for young female athletes (see, e.g., Female Athlete Triad, Switzerland. Magazine for "Sportmedizin und Sporttraumatologie" 48 (3), 119-132 (2000), the content of which is incorporated herein by reference). For the treatment of osteoporosis according to the invention, it is essential that the presence of osteoporosis can reliably be diagnosed. There are indeed a number of ways for the diagnosis of osteoporosis and the prediction of bone fracture. The most widely used is dual energy X-ray absorptiometry (DXA). DXA scans are primarily used to measure the areal bone mineral density. An even more reliable method, yielding directly the volume density of a bone, is computed quantitative computer tomography (see for example http://en.wikipedia.org/wiki/Dual-energy X-ray absorptiometry. the entire content of which is hereby incorporated by reference)(See FIGS. 11, 12A, 12B and 13). These figures are referred to as a matter of background information and show, in FIG. 12, a DXA scanner adapted to scan the body to evaluate bone mineral density using dual-energy X-ray absorptiometry. FIGS. 12A and 12B are schematic views of a DEXA assessment of bone mineral density of the femoral neck and of the lumbar spine, respectively. FIG. 13 is the output of a full body scan is shown on a screen of a DEXA scanner.

One way to prophylactically treat osteoporosis is through the use of pharmaceuticals, which, besides being of limited effectiveness, are often hampered by serious side effects. A better solution seems, therefore, to be the use of prophylactic implants, enhancing the mechanical stability of the bone, thus providing a local and not a systemic way to address the problem. Such implants are generally introduced in either of a number of ways, such as (1) through a bore in the greater trochanter along the femoral neck axis (see for example U.S. Pat. No. 6,679,890 to Margulies and U.S. Pat. No. 6,319,255 to Grundei, the contents of which are hereby incorporated by reference); (2) through the intramedullary canal of the proximal femur (see for example U.S. Pat. No. 8,012,155 to Prygoski, the content of which is hereby incorporated by reference); (3) through a bore in Ward's triangle (see for example US 2009/0112210 to Philippon, the content of which is hereby incorporated by reference).

It is a general feature of the prior art that the bore has been made from the side, i.e. in a plane containing the femur body, the femoral neck and the femoral head. This, however, may damage the surrounding soft tissue.

What is needed is a reliable, simple method of reinforcing osteoporotic bone. What is needed is a method that is devoid of any of the systemic side effects of drugs, while being minimally invasive to avoid soft tissue damage.

SUMMARY OF THE INVENTION

A system, device and method is provided for the treatment of osteoporotic bones, especially of the femoral neck. The system includes a device for positioning the implant under optical and X-ray control, an implant and an applicator for screwing and expanding the implant. The implant includes an insert body and an expansion tube with cut-outs and slits defining legs. The legs expand radially through windows in the insert body when the expansion tube is pushed against the sloped distal portion of the insert body. The expansion process may be better ensured by an anti-rotation device, which prevents the expansion tube from rotating within the insert body. The applicator and implant are provided with means preventing cold welding during the implantation process.

It is another object of the invention to provide a means for minimal invasiveness during the introduction of a hip implant.

It is another object of the invention to provide an expandable structure within bone, which is able to guide healthy cortical bone to less functional trabecular bone areas, thereby enhancing its stability.

It is another object of the invention to provide accurate and simple positioning of a hip implant.

It is another object of the invention to provide a hip implant and an applicator for its positioning, insertion and expansion.

It is another object of the invention to provide a method for the creation of a hip implant under optimal visual and X-ray control.

BRIEF DESCRIPTION OF THE DRAWINGS

FIG. 2A is a side view of an unassembled hip implant.

FIG. 2B is a perspective view of an unassembled hip implant. FIG. 2C is a perspective view of an assembled hip implant before expansion. FIG. 2D is a perspective view of an assembled hip implant after expansion.

Those skilled in the art will appreciate that elements in the Figures are illustrated for simplicity and clarity and have not necessarily been drawn to scale. For example, dimensions may be exaggerated relative to other elements to help improve understanding of the invention and its embodiments. Furthermore, when the terms 'first', 'second', and the like are used herein, their use is intended to distinguish between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known to the inventors as of the filing date hereof. Consequently, changes may be made in the arrangement and/or function of any of the elements described in the exemplary embodiments disclosed herein without departing from the spirit and scope of the invention.

In the following, a complete system of hip implants and its use will be described. The system comprises the implant itself, and additional devices or "applicators" used for precise positioning of the implant.

Figure 1A:
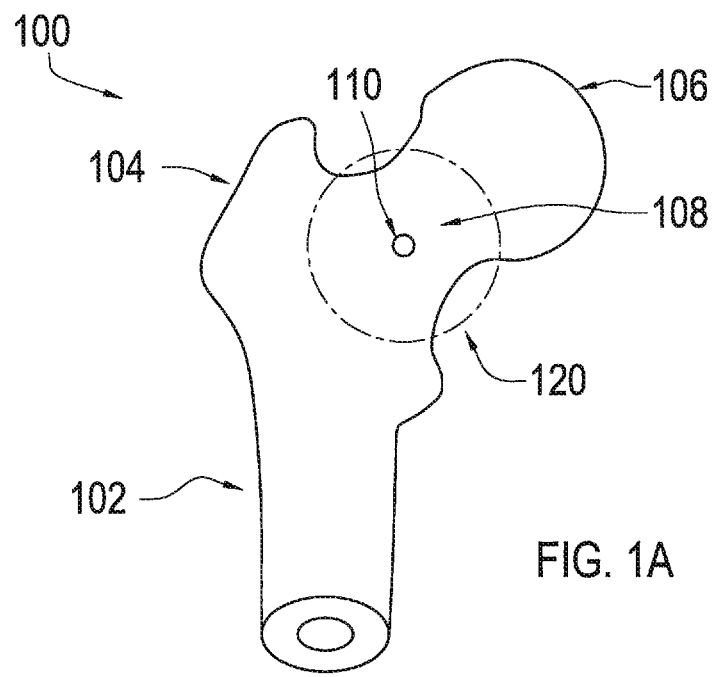
FIG. 1A is a schematic view of the positioning of a hip implant in the region of Ward's triangle.

Referring now to FIG. 1A, part of a femur 100 is shown, with femur body 102, greater trochanter 104, femur head 106 and femur neck 108. The bore 110 for a hip implant is drilled through the cortical bone over Ward's triangle region of the femur neck, in a direction perpendicular to the plane containing femur body 102, femur neck 108 and femur head 106. According to the invention, this positioning of the bore has proven to be minimally invasive, as it minimizes soft tissue damage while placing the implant. The size of bore 110 is in the range of 4 to 8 mm, preferably about 5 mm. Circle 120 indicates the maximal reach in terms of lateral expansion of the implant. The diameter of the circle 120 is, for example, in the range of 4.6 cm, and it may be obtained using an implant having 1.9 cm long legs (see for example FIGS. 2 and 5). In another embodiment (not shown) having longer legs, regions of the femoral head 106 or the greater trochanter 104 may be reached.

Figure 1B:
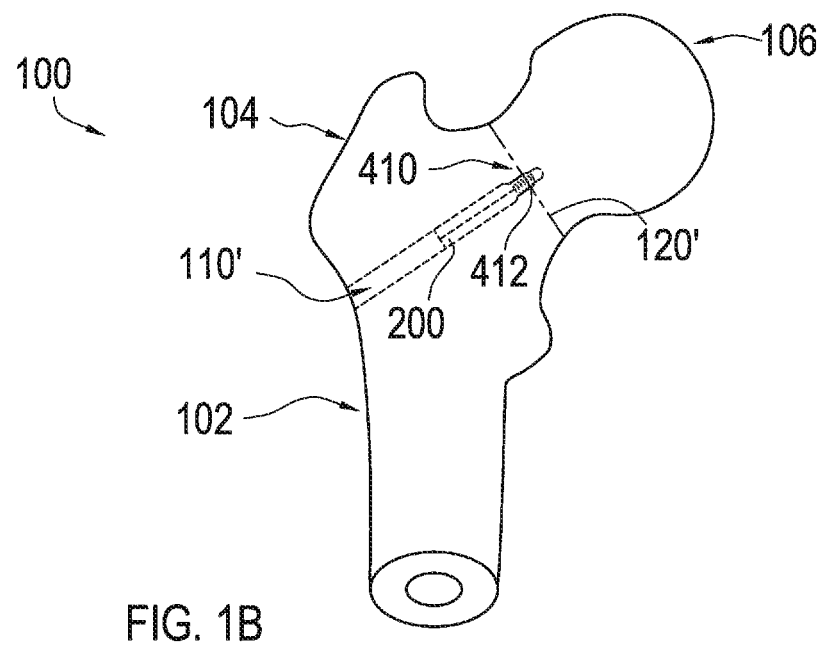
FIG. 1B is a schematic view of an alternative positioning of a hip implant into the region of Ward's triangle.

As an alternative placement strategy illustrated in FIG. 1B, the hip implant 200 of the present invention may be inserted into the region of the femoral neck 108 from the greater trochanter region 104 of the femur 100. In accomplishing this placement strategy, a bore 110' is made from the greater trochanter 104 toward the femoral head 106 axially to the femoral neck 108 and perpendicular to a plane 120' of the cross-section of the neck 108. Using this positioning strategy, the regions of the femoral head 106 and the greater trochanter 104 may also be reached by adjusting the depth of the bore 120'.

Referring now to FIGS. 2A-2B, the unassembled components of a hip implant 200 are shown, along with an implant in its assembled state (see FIG. 2C) and finally in expanded form (see FIG. 2D). Referring in particular to FIGS. 2A-2B, the main components are made up of two parts, a guiding insert body 210 which is screwed into the bore 110, and an expansion tube 230 with slits 232 and cut-outs 233, which, when deformed, form at least two and preferably four or more legs 234. FIG. 2A shows an optional cap 240 for sealing the implant at its proximal end. The insert body 210 is made up of a proximal portion 217 and a distal portion 216 connected at the distal end 211 of the proximal portion 217 by arms 213 to a proximal end 218 of the distal portion 215. The proximal portion 217 of the insert body 210 has two screw threads, the first thread 212 for screwing the implant into bore 110, and the second thread 222, of only a few turns located at a proximal end 215 of the proximal portion 217, for fixing the implant to the applicator 300, 400 used for mounting the implant (see also FIGS. 3A-3C and 4). The arms 213, extending between the proximal portion 217 of the insert body 210 and the distal portion 216, define windows 214. The proximal surface 218 of the distal portion 216 of the insert body 210 is preferably sloped. The angle of the sloped surface 218 is preferably about 45 degrees with respect to the axis of insert body 210.

During assembly of the implant 200, 500, the expansion tube 230 may be slid into hollow insert body 210 until legs 234 make contact with the sloped surface 218 of distal portion 216, the deflection plate, as shown in FIG. 2C. Upon pushing expansion tube 230 further into insert body 210, the legs 234 are deflected outside of windows 214 by being outwardly directed against the sloped surface 218. This process initiates the lateral expansion of the legs 234 of the implant 200, 500, which is shown in FIG. 2D in its final form. The extent to which legs 234 extend laterally depends on a number of parameters, such as the material, for example stainless steel or titanium, and thickness of expansion tube 230, and the sloped surface 218 of the distal portion 216, as well as the angle of the slope.

The insert body 210 may contain a flange 224 between screw threads 212 and 222. As shown in FIG. 2B, flange 224 optionally has two flat regions 226 on opposite sides of insert body 210. According to the invention, the flat regions 226 are provided to take up the torque applied by the applicator to insert body 210 while the insert body is screwed into bore 110 (see also FIG. 3). This feature minimizes the risk of cold welding of the applicator 300, 400 to the insert body 210 during screwing of the implant 200, 500 into bore 110.

Figure 3A:
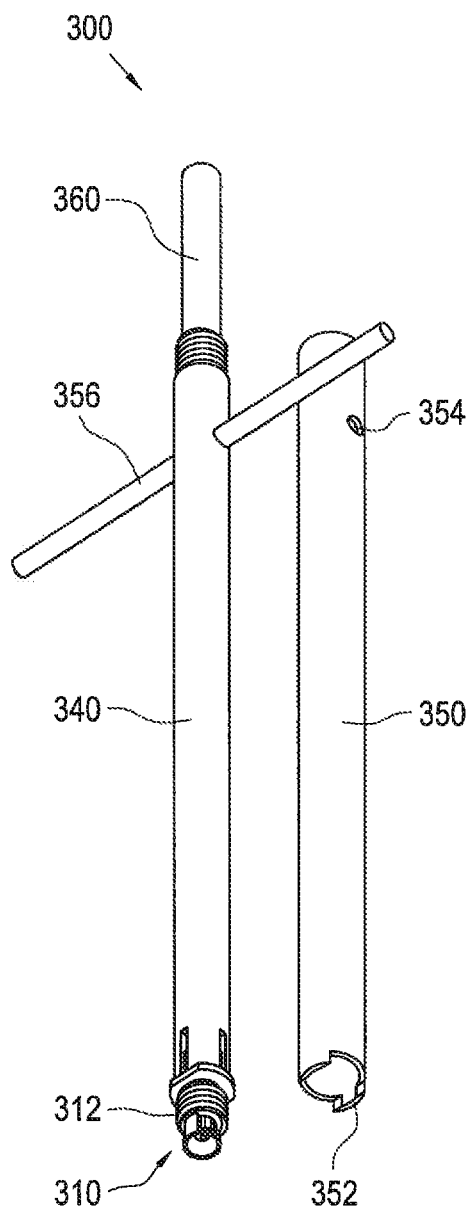
FIG. 3A is a perspective view of an applicator for inserting a hip implant.
Figure 3B:
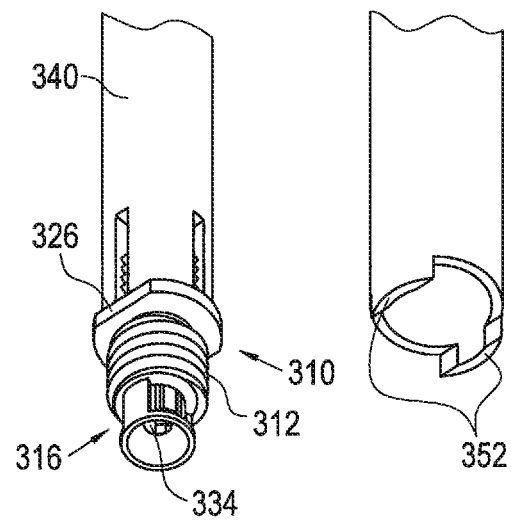
FIG. 3B is a detailed perspective view of components of the applicator.
Figure 3C:
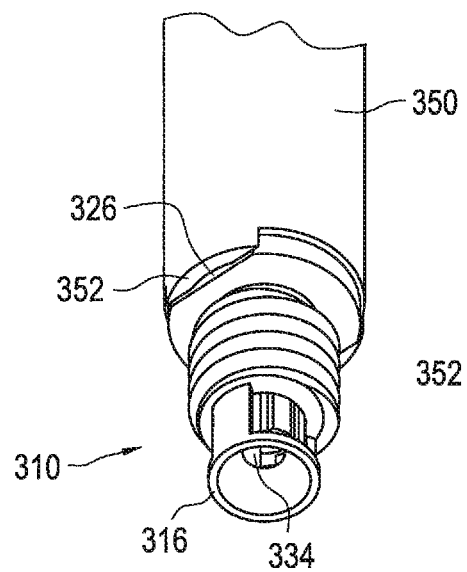
FIG. 3C is a detailed perspective view of a hip implant mounted on an assembled applicator.

Referring now to FIG. 3, a first embodiment 300 of an applicator 300 for screwing the implant 200 into bore 110 may comprise a tube 340 into which guiding insert body 210, 310 can be screwed. In order to avoid the torque being applied to screw thread 222 during screwing the sleeve into the cortical bone, which may run the risk of cold welding the threads, a second tube 350, the inner diameter of which exceeds the outer diameter of tube 340, is slid onto tube 340. The end facing the implant of tube 350 may contain extensions 352 on opposite sides, as shown in FIGS. 3A-3B. These extensions interface with the flat regions 326 of insert body 210, 310, as shown in FIG. 3C. The torque exerted during screwing the guiding sleeve into the cortical bone may hence be applied to the flat regions 326, whereby the risk of cold welding of any parts is minimized. Torque may be applied by means of lever 356 which may be inserted into holes 354 in tube 350. Larger holes in inner tubes 340, 360 help ensure that the torque exerted by lever 356 is exerted primarily on the outer tube 350. Torque is also applied on tube 340, but only to a small extent. It is important to note that the torque is not transmitted primarily to the screw thread but instead to the flats 226.

Once the insert body 210 has been properly screwed into the bore and the lever 356 removed, an innermost tube 360 may serve to push expansion tube 230 towards the sloped surface 218 of the distal portion 216, 316, thereby expanding legs 234, 334 into the inner space of the femur neck 108.

Figure 4:
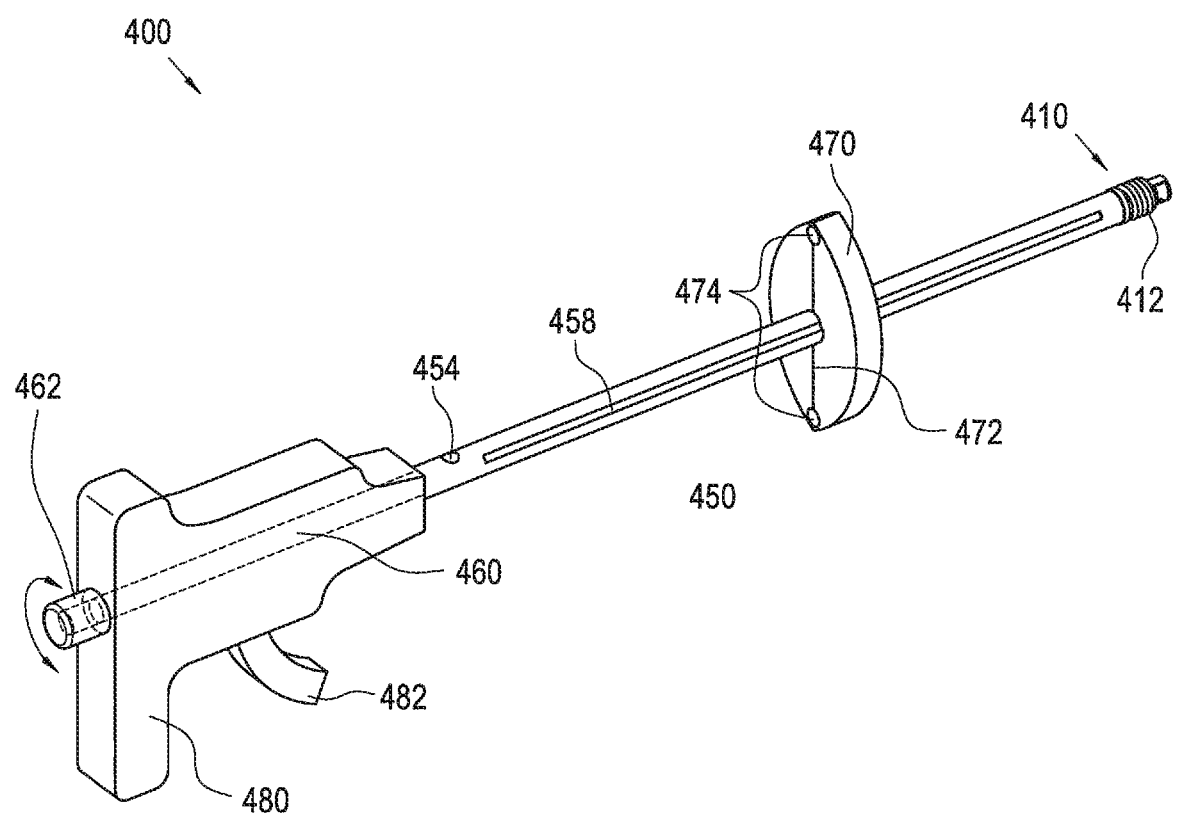
FIG. 4 is a perspective view of the applicator with a mounted implant and integrated positioning control.

Referring now to FIG. 4, another embodiment 400 of an applicator provides a more accurate positioning of the implant 200, 500 under optical and X-ray control. Here, the outermost tube 350, 450 exerting the torque on insert body 310, 410 during the torquing of screw thread 312, 412 into the cortical bone may contain guiding grooves 458. These guiding grooves keep slider 470 from rotating around the axis of the applicator as it slides along tube 350, 450. Slider 470 may contain optical marks 472 facing the surgeon during the operation, allowing him to position legs 234, 334 accurately with respect to the axis of femoral neck 108. Additional positioning control may be accomplished by providing X-ray absorbing material 474 aligned with optical marks 472 of slider 470. This permits direct observation by X-rays in addition to the visual method of positioning the implant. Applicator 400 may furthermore be equipped with lever 482 by means of which the innermost tube 460 can be pushed against expansion tube 230 in order to expand legs 234, 334 of expansion tube 230. Removable cap 462 screwed onto the innermost tube 460 may prevent pushing of expansion tube 230 by any accidental movement of lever 482.

Figure 5A:
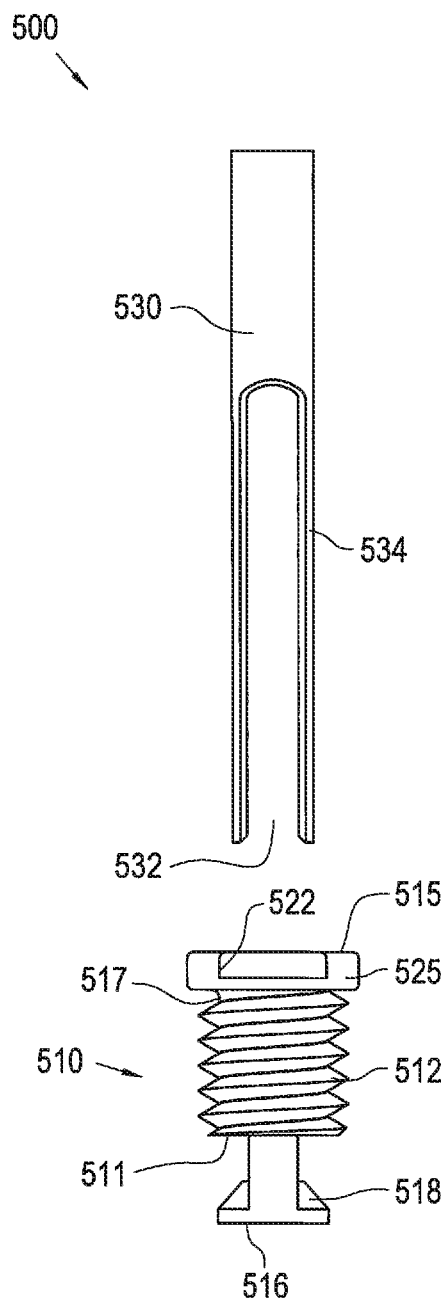
FIG. 5A is a side view of another embodiment of a hip implant in unassembled form.
Figure 5B:
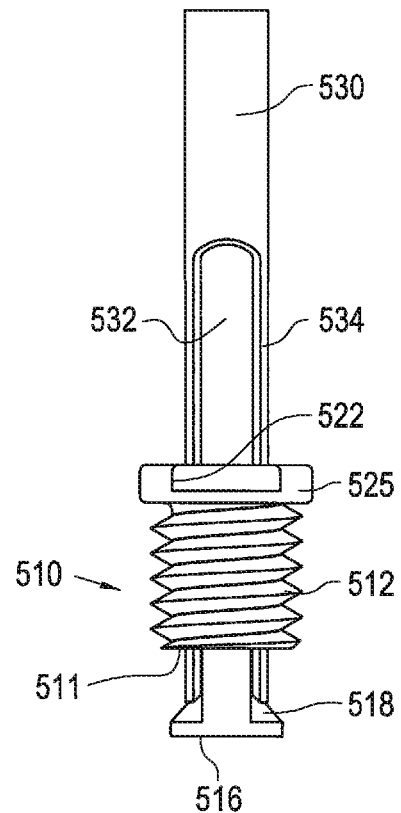
FIG. 5B is a side view of the embodiment of FIG. 5A, in an assembled form.

Referring now to FIG. 5, another embodiment 500 of insert body 510 may contain a section 525 above screw thread 212, 312, 512 which may be shorter than the corresponding section of insert body 210, 310. Accordingly, the screw thread 522 used for attaching insert body 510 to applicator 400 may be located on the inside of section 525, as shown in FIGS. SA-SB. This has the advantage of causing even less soft tissue damage during implantation, because of a less protruding outermost tube of applicator 400 (see also FIG. 6). This design also allows a more shallow structure outside of the femoral neck, which advantageously reduces irritation of soft tissue.

Figure 6A:
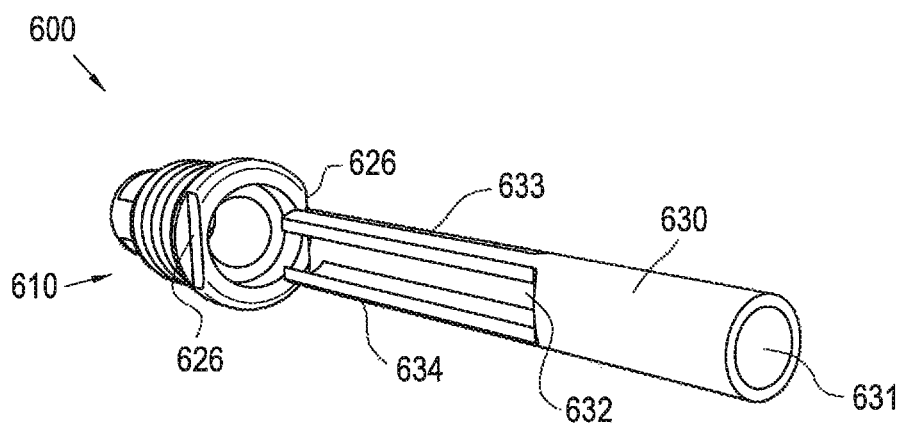
FIG. 6A is a perspective view of the embodiment of FIG. 5A in unassembled form.
Figures 6B, 6C:
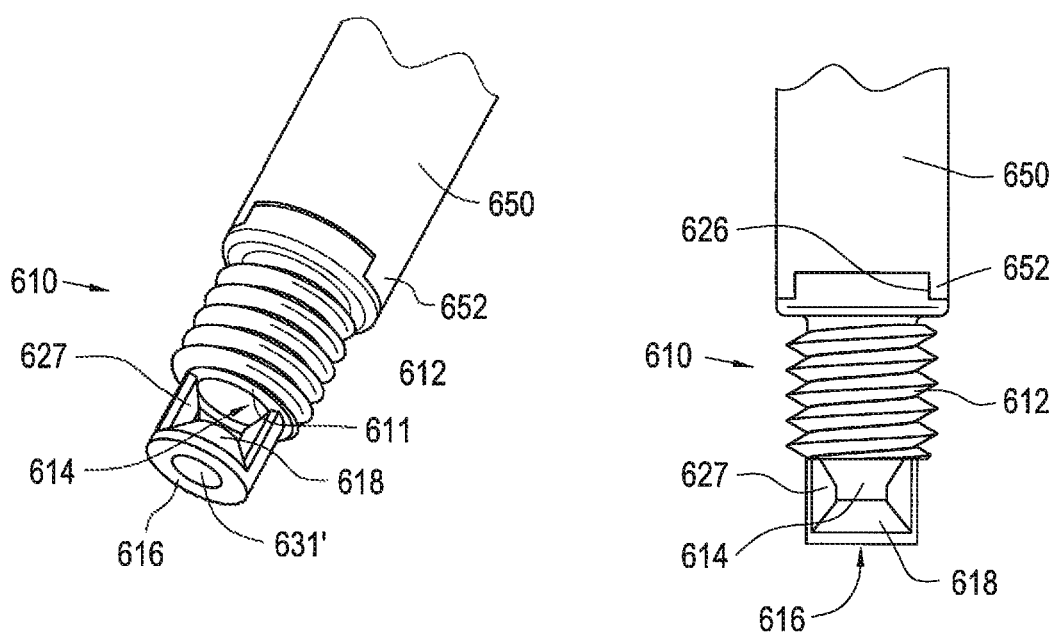
FIG. 6B is a perspective view of the embodiment of FIG. 5A mounted on the applicator.
FIG. 6C is a side view of the embodiment of FIG. 5A mounted on the applicator.

Referring now to FIG. 6A-6C, this embodiment of the insert body 510, 610 optionally incorporates an anti-rotation device 627, which in one embodiment is essentially a specially shaped frame of window 214, 614, as shown in FIGS. 6B-6C. This shape prevents expansion tube 230, 530, 630 from rotating while it is pushed into the insert body and during the positioning of the implant in the bone. As a result, legs 234, 534, 634 are free to expand through window 214, 614, while expansion tube 230, 530, 630 is pushed against the inclined or sloping surface 218, 518, 618 of distal portion 216, 516, 616. The flats 626 of section 525 are formed to absorb the torque exerted by the extensions 652 of applicator 400 while the insert body 510,610 is screwed into the bore 110.

In other embodiments insert body 210, 310, 410, 510, 610 of the implant 200, 500 may be fastened in different ways to applicator 300, 400 rather than by screw thread 222, 522. The fastening mechanism may, for example, comprise a bayonet lock, a clamping fastener, or any other means by which the applicator is detachable from the insert body of the implant after the latter has been screwed into bore 110 and expanded.

Figure 7A:
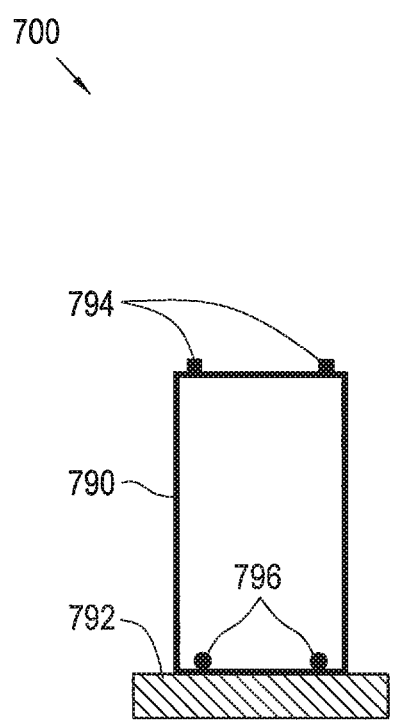
FIG. 7A is a side view of a device for controlling the position of hip implants, before implant hole drilling and implant positioning.
Figure 7B:
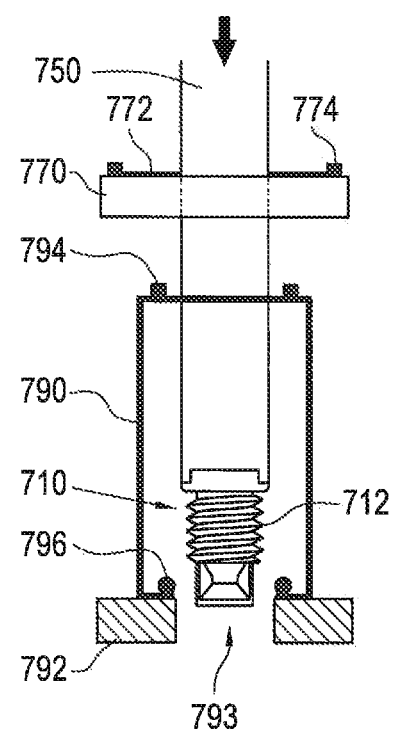
FIG. 7B is a side view of the device of FIG. 7A for controlling the position of hip implants, after implant hole drilling and during positioning.

Referring now to FIG. 7, the system for forming a hip implant may comprise an additional device 700 for precise implant positioning. Device 700 may comprise a guiding tube 790 which may be placed on the cortical bone 792 at the chosen location of bore 110, 793, as shown in FIG. 7A. Guiding tube 790 is provided with optical markers with respect to which optical markers 472, 772 on slider 470, 770 of the applicator are aligned in order to allow precise positioning of the implant, as shown in FIG. 7B. Guiding tube 790 may furthermore be equipped with markers 796, made from X-ray absorbing material, aligned with the optical marks 794. During the operation, markers 796 may be aligned under X-ray control with X-ray markers 474, 774 on slider 470, 770 of the applicator, allowing for even better control of the process of implant formation and positioning. In addition, alignment of optical markers 794 with the guiding grooves 458 or other optical lines, marks, etc. on tube 350, 450, 650 without the use of the slider 470, may aid in positioning the implant.

Figure 8:
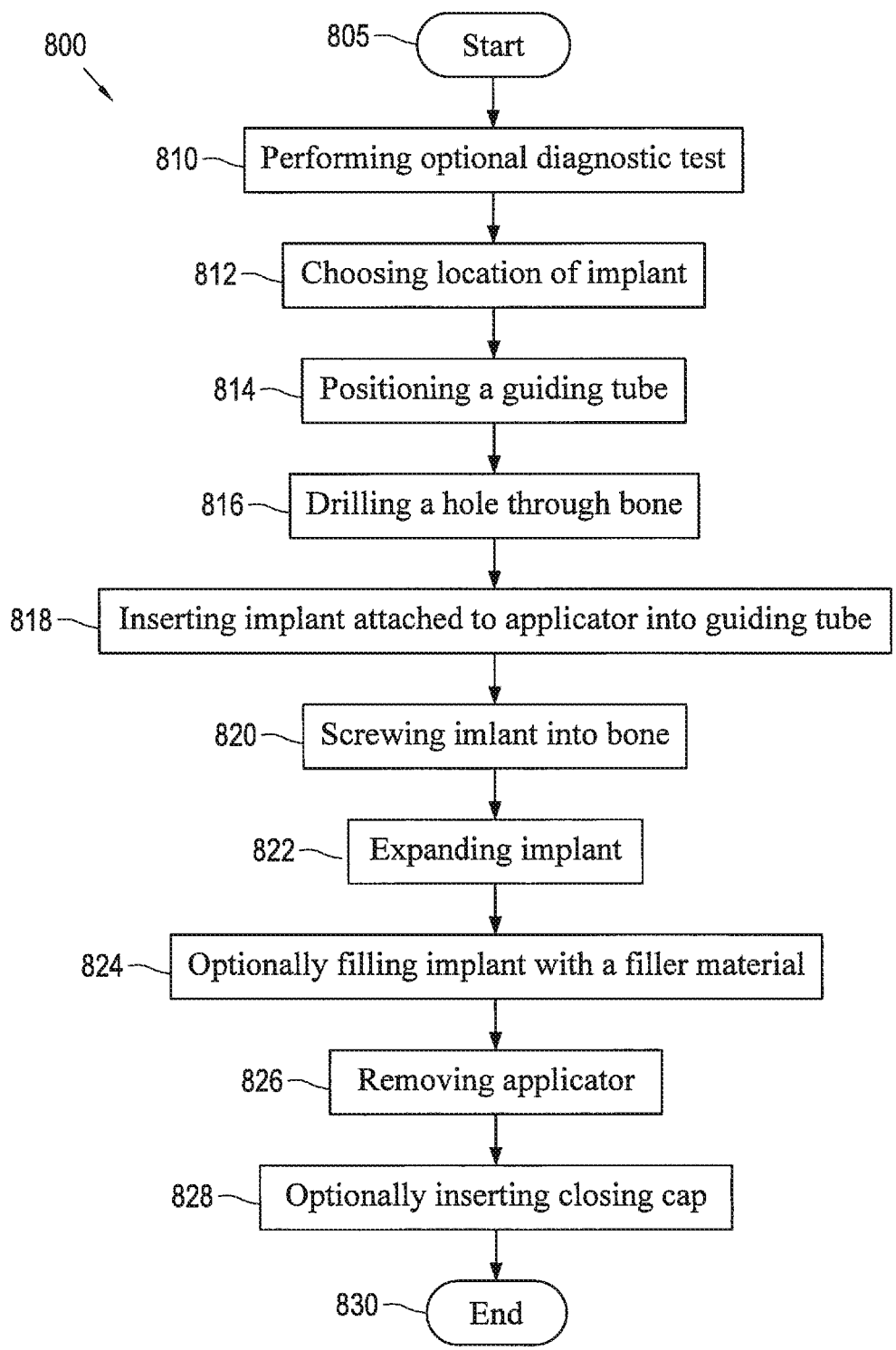
FIG. 8 is a method for inserting and forming a hip implant.

Referring now to FIG. 8, a method 800 for the use of the system for forming a hip implant includes any one of a list of steps: in an optional first step 810, performing diagnostic tests for osteoporosis; in a second step 812, choosing the location of the implant; in a third step 814, placing a guiding tube 790 for positioning control; in a fourth step 816; forming the bore under precise positioning control; in a fifth step 818, inserting the implant by means of an applicator through the guiding tube; in a sixth step 820, screwing the implant into the bone; in a seventh step 822, expanding the implant; in an eight step 824, optionally filling the implant and adjacent cancellous bone regions by a filler material (including calcium phosphate, bone cement or the like) preferably through the applicator; in a ninth step 826, removing the applicator; and, in a tenth step 830, optionally inserting a cap for sealing the implant.

The assembled hip implant 200, 500 has an aperture or bore 231, 631, 631' passing through its central axis. When the hip implant 200, 500 device is installed, this central bore 231, 631, 631', it can allow access to the cancellous region of the bone. Utilizing the aperture or bore 231, 631, 631', other prosthetics or instruments (e.g., a trocar) and/or biological agents (e.g., a bone growth biologic) can be inserted into the implant site.

Figure 9:
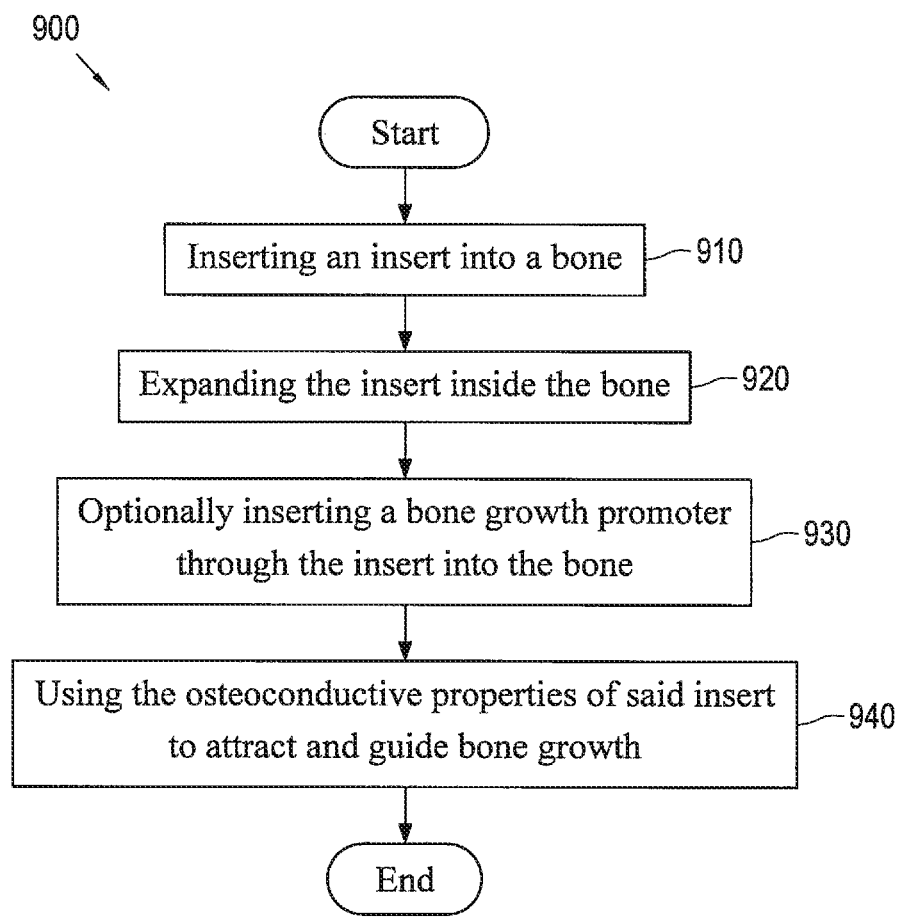
FIG. 9 is . . . a method of the invention for treating osteoporosis.

Referring now to FIG. 9, in another embodiment, a method of treating osteoporosis is provided which directs healthy cortical bone to less functional trabecular bone areas, thereby substituting the less functional trabecular areas of the bone with healthy bone mass, the method including several steps. In a first step 910, the insert is inserted into a bone. In a second step 920, the insert is expanded inside the bone. In a third step 930, a bone growth promoter is optionally inserted through the insert into the bone. In a fourth step 940, the osteoconductive properties of the insert are used to attract and guide bone growth. The osteoconductive properties of said insert may be enhanced by surface treatment or coating of the insert with bone growth enhancing substances or structures. Additionally, the insertion and making of the implant provides a bridging from cortical to trabecular bone areas in a flexible way. Mechanical force from the cortical bone areas may be transduced to the implant body and legs, thereby stimulating bone growth by the intrinsic property of bone to rebuild and restructure at sites of mechanical loading. By designing and making of said implant in a semi-rigid, rather than rigid way, stress shielding with all negative consequences on the stability of the bone is avoided. The rationale behind this is, that the quality of bone can deteriorate in the vicinity of implants due to stress shielding. Because bone is a dynamic tissue, it reacts on loading by building up tissue and gets weaker, when not loaded. By repeatedly transducing the force from cortical areas (via the insert and legs) to trabecular areas, these areas may react by bone growth stimulation/or the ingrowth from cortical areas may be of better quantity and quality.

Figure 10A:
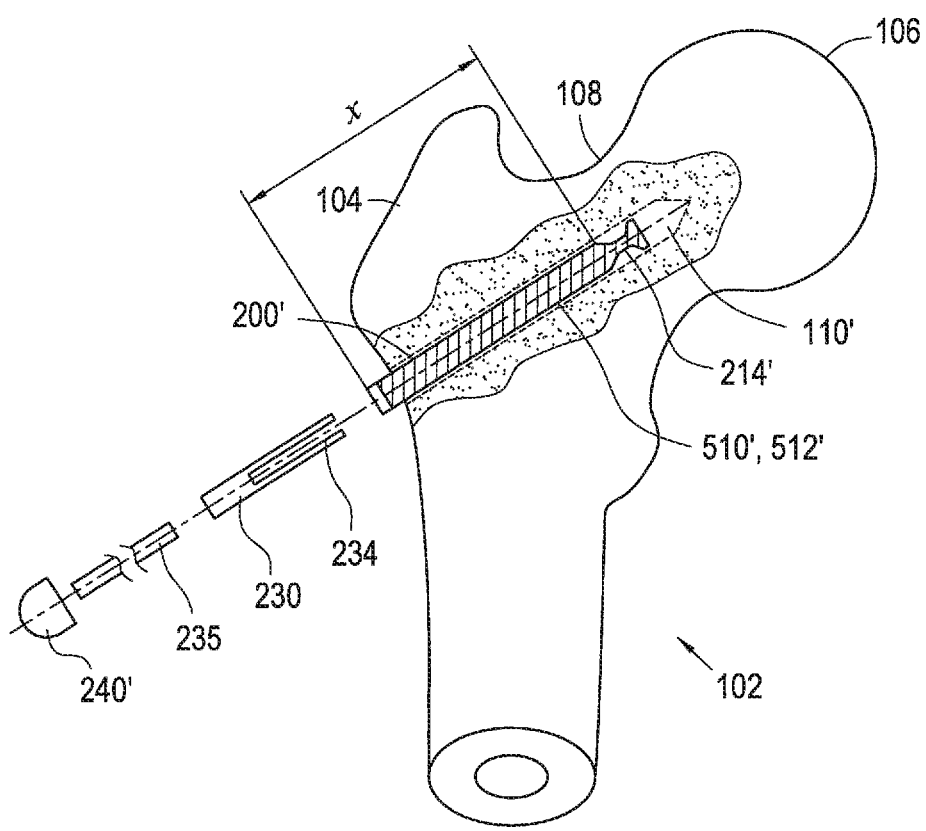
FIG. 10A is a schematic, exploded view showing more detail of the alternative placement strategy illustrated in FIG. 1B.
Figure 10B:
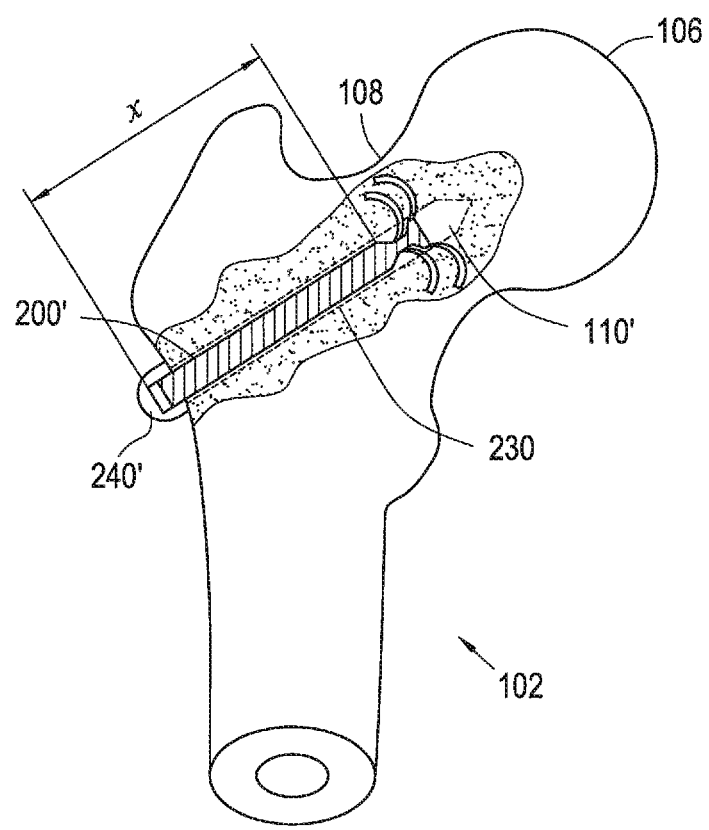
FIG. 10B is a schematic, assembled view showing more detail of the alternative placement strategy illustrated in FIG. 1B.
Figure 11:
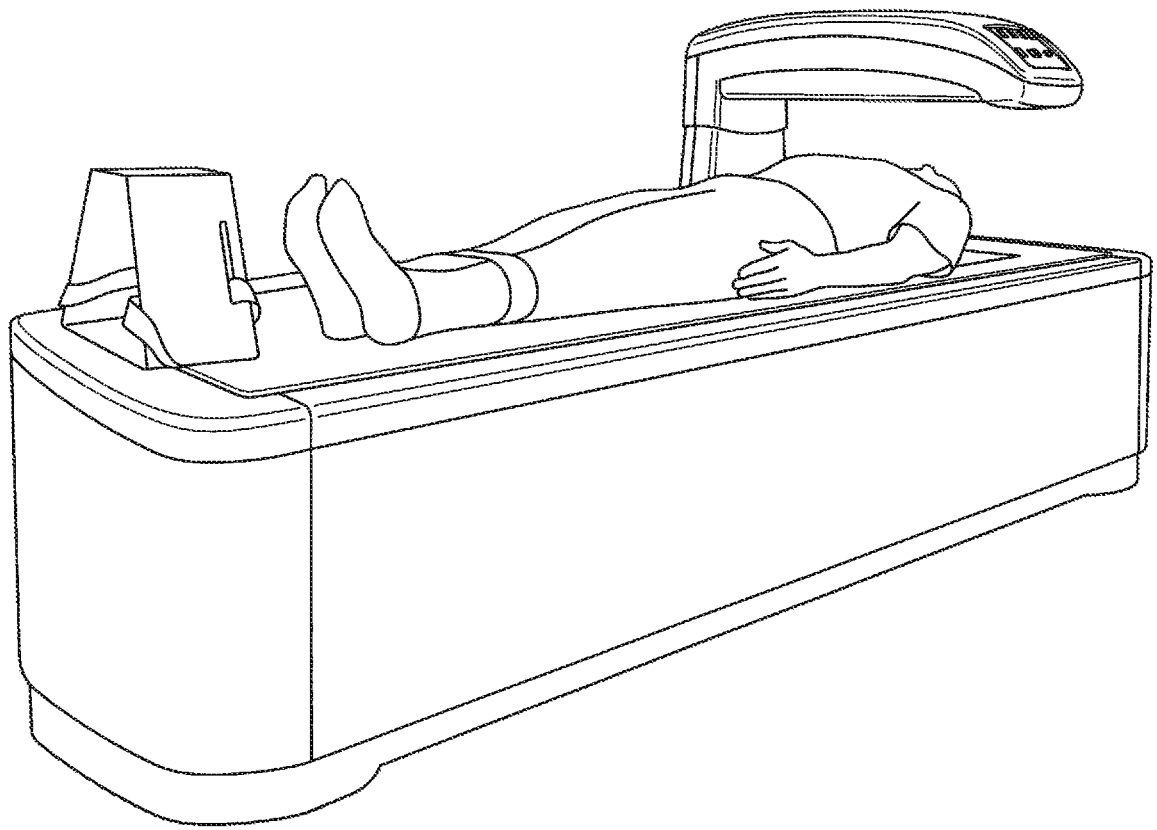
FIG. 11 is a device used for measuring bone density using dual-energy X-ray absorptiometry.
Figure 12A:
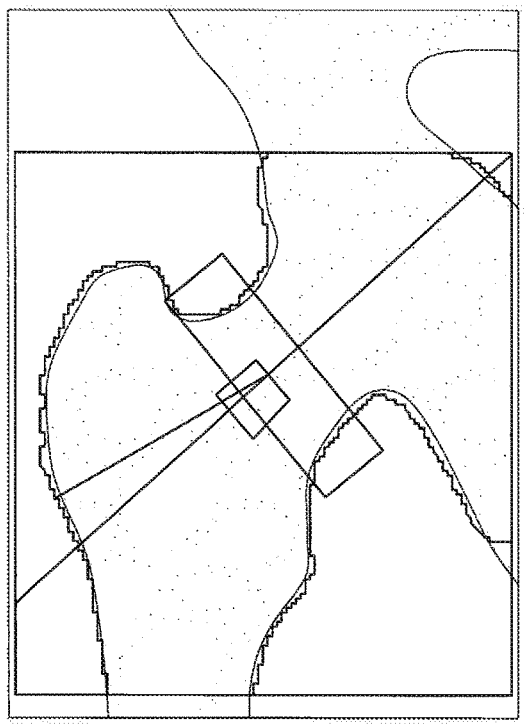
FIGS. 12A and 12B are schematic views of a DEXA assessment of bone mineral density of the femoral neck and of the lumbar spine, respectively.
Figure 12B:
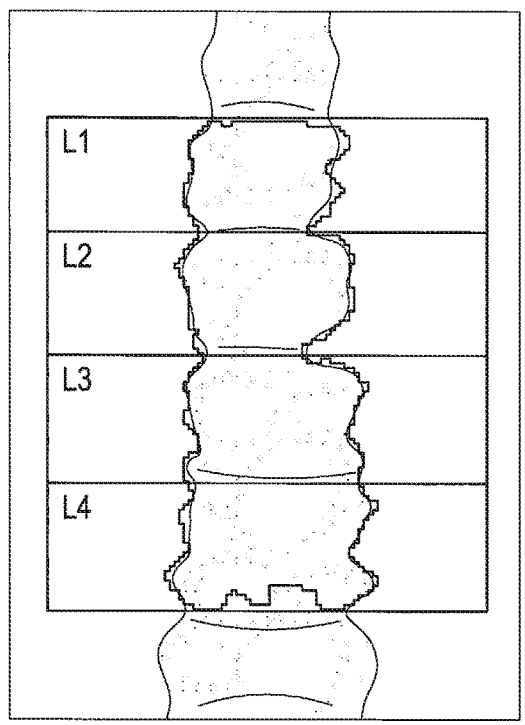
Figure 13:
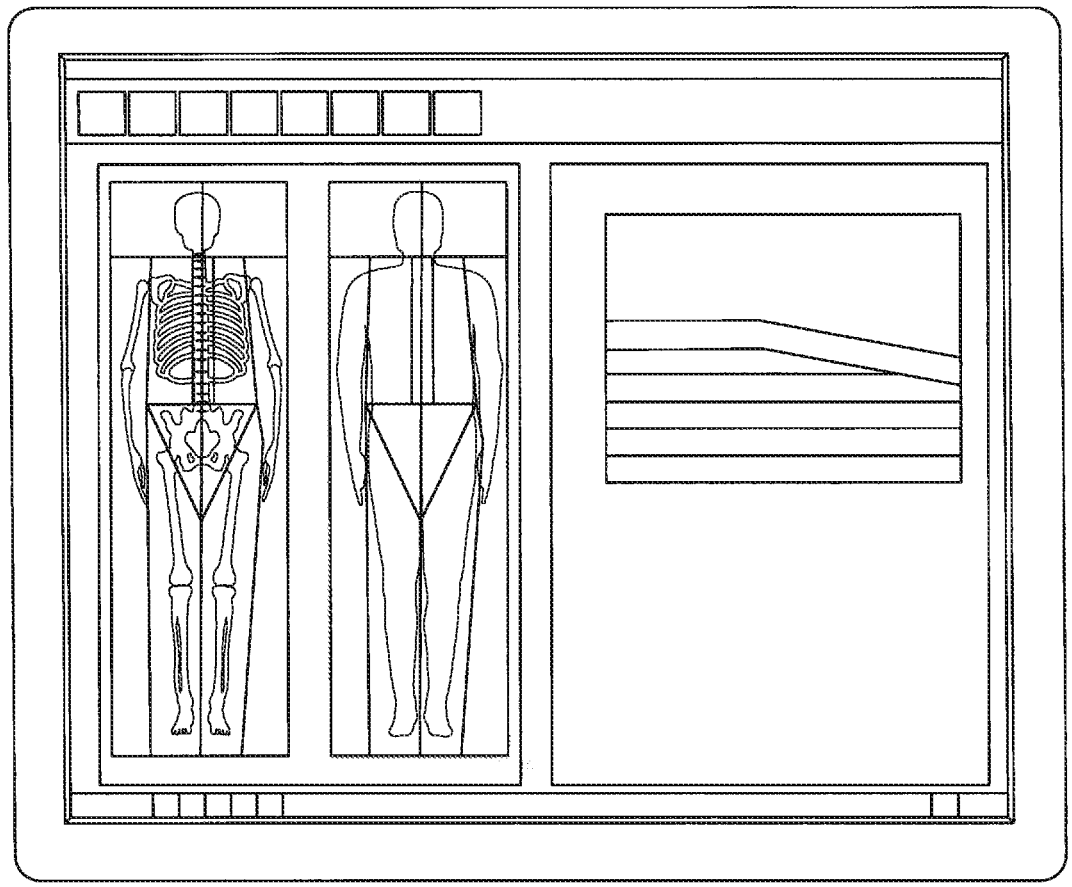
FIG. 13 is a schematic view of a full body scan appearing on a screen of a DEXA scanner.

Referring now to FIGS. 10A and 10B, which show more detail of the alternative placement strategy illustrated in FIG. 1B, the hip implant 200' of the present invention having a body 510' elongated to a length X (to suit the patient's particular bone size) when compared to the other embodiments presented herein, may be inserted such that the legs 234' may be extended into the region of the femoral neck 108 by insertion of the implant 200' from the greater trochanter region 104 of the femur 100. Threads 512' may extend along the entire body 510' of the implant 200'. However, only a few threads 512' are required to be able to drive the insert 200' into the desired location. Windows (not shown) are optionally added along the body 510' to allow leaching out of bone growth promoting substances which may be placed therein. In accomplishing this placement strategy, a bore 110' is made from the greater trochanter 104 toward the femoral head 106 axially to the femoral neck 108 and perpendicular to a plane 120' of the cross-section of the neck 108. The insert body 510' is inserted in the bore 110' and the tool described in FIG. 3A-3C drives the insert body to the desired position, where the windows 214' are adjacent the femoral neck area 108. The expansion tube 230 is then inserted, followed by a spacer 235. The spacer 235 may be made such that it is porous to contain bone growth promoting compounds. The spacer 235 may also be a power metal pressed part, pressed together with bone growth promoting agents. This spacer 235 allows use of a standard length expansion tube 230 and permits the extrusion of the expansion tube 230 through the windows 214', such that the legs 234' extend through the windows 214', breaking up the trabecular bone and allowing bone regrowth and reinforcement of the femoral neck 108. A cap 240' may be installed over the end of the insert 230, to protect against damage to adjacent soft tissue.

It should be appreciated that the particular implementations shown and herein described are representative of the invention and its best mode and are not intended to limit the scope of the present invention in any way. For instance, tapping in of the innermost tube 360, 460 into the guiding insert body 210, 510 with a rod- or trocar-like instrument (not shown) and a mallet (not shown) is an alternative method for expanding the implant 200,500. Of course, there are any number of different ways to press the expansion tube 230, 530 into the guiding insert body 210, 510 such as by turning a thread which drives the expansion tube therein. In addition, the shape of the surface 218, 518 of the deflection plate 216, 516 may comprise any shape suitable for deflecting and even directing the deflection of the legs 234, 534. For example, the selection of an appropriate shape for the legs 234, 534 and the deflection plate 216, 516 may be made to cause the legs to spiral through the cancellous bone, in order to create a larger cavity.

Moreover, the system contemplates the use, sale and/or distribution of any goods, services or information having similar functionality described herein.

The specification and figures should be considered in an illustrative manner, rather than a restrictive one, and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements that includes not only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures, which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-a-vis the public or third parties, no express or implied license is granted to prepare derivative works based on this patent specification, inclusive of the appendix hereto and any computer program comprised therein.

Additional features and functionality of the invention are described in the claims appended hereto. Such claims are hereby incorporated in their entirety by reference thereto in this specification and should be considered as part of the application as filed.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without a corresponding use of the other features. Accordingly, it is appropriate that the foregoing description be construed broadly and understood as being illustrative only, the spirit and scope of the invention being limited only by the claims that ultimately issue in this application.

What is claimed is:

1. A system for implanting a bone implant, the system including the bone implant and an applicator, the bone implant comprising:
   a) an insert body having a proximal end, a mid-point, and a distal end, the insert body further having an externally threaded proximal portion adjacent the proximal end of the insert body, the proximal portion configured to affix the insert body to cortical bone and a distal portion separated from the proximal portion by at least two arms defining windows therebetween, and
   b) an expansion tube fitting into said insert body, wherein cut-outs define at least two legs;
   the applicator being configured to be attached to the insert body for affixing the insert body into the bone prior to pressing the expansion tube into the insert body, the pressing splaying the at least two legs in a distal direction so as to agitate cancellous bone.

2. The system of claim 1 further comprising a positioning device configured to guide said applicator into a bore in the bone.

3. The system of claim 1, wherein said distal portion has a slope configured to deflect said legs radially outwards through said windows when said expansion tube is pushed against said slope.

4. The system of claim 1, wherein said insert body comprises an anti-rotation device which prevents said expansion tube from rotating when forcing said legs to be expanded through said window when said expansion tube is pushed against said slope.

5. The system of claim 1, wherein said insert body is configured to be attached to said applicator by a device selected from one of a group of devices consisting of a screw thread, a bayonet lock and a clamping fastener.

6. The system of claim 1 comprising a feature which avoids cold welding of said applicator to said insert body during screwing said sleeve into the said bore.

7. The system of claim 1, wherein said applicator and said insert body include a device for relative position control, including optical marks and X-ray marks.

8. The system of claim 1, wherein the applicator is configured to insert the insert body and expansion tube of the implant into a guiding tube, to screw said implant into the bone, and to expand said implant.

9. The system of claim 1, wherein the insert body is dimensioned so that, upon insertion in a region of the Ward's triangle on the femoral neck, the proximal portion of the insert body affixes to the cortical bone on one side of the femoral neck and the distal portion extends to the cancellous bone region of the femoral neck.

10. The system of claim 1, wherein the at least two legs of the expansion tube have at least one slit or scoring, which facilitates splitting of a leg into two partial legs as the expansion tube is pressed into the insert body, thereby splaying the legs out distally.

11. The system of claim 1, wherein the at least two legs splay out in response to deflection by a deflection surface on the insert body.

12. The system of claim 1 wherein the insert body further includes a flange that is configured to interface with the applicator.

13. A bone implant comprising:
   (a) an insert body having a proximal end, a mid-point, and a distal end, the insert body further having an externally threaded proximal portion adjacent the proximal end of the insert body, the proximal portion configured to affix to cortical bone and a distal portion separated from the proximal portion by at least two arms defining windows therebetween, the insert body further including a flange at the proximal end configured to interface with an applicator; and
   (b) an expansion tube fitting into said insert body, wherein at least two slits define at least two distally directed legs.

14. The bone implant of claim 13, wherein an aperture passes therethrough, to allow access, when implanted, to a cancellous region of a bone.

15. The bone implant of claim 13, wherein an aperture passes therethrough, to allow a biological agent to be inserted into the implant site.

* * * * *